United States Patent [19]
Lavaire et al.

[11] Patent Number: 5,786,469
[45] Date of Patent: Jul. 28, 1998

[54] 1-C-PERFLOUROALKYL GLYCOSIDES, PREPARATION PROCESS AND USES THEREOF

[75] Inventors: Sandrine Lavaire; Richard Plantier-Royon, both of Reims; Charles Portella, Cormontreuil, all of France

[73] Assignee: CECA S.A., France

[21] Appl. No.: 879,364

[22] Filed: Jun. 20, 1997

[30] Foreign Application Priority Data

Jun. 20, 1996 [FR] France .................. 96 07692

[51] Int. Cl.[6] ............... C07H 7/02; C07H 1/00; A62D 1/00
[52] U.S. Cl. ............... 536/122; 252/2; 252/3; 536/1.11; 536/4.1; 536/18.5; 536/124
[58] Field of Search .............. 536/1.11, 4.1, 536/18.5, 122, 124; 252/2, 3

[56] References Cited

U.S. PATENT DOCUMENTS

| | | | |
|---|---|---|---|
| 4,855,460 | 8/1989 | Tordeux et al. | 549/308 |
| 4,957,904 | 9/1990 | Falk et al. | 514/24 |
| 4,999,119 | 3/1991 | Norman et al. | 252/3 |
| 5,207,932 | 5/1993 | Norman et al. | 252/3 |

OTHER PUBLICATIONS

Luo et al. *Chin. Chem. Lett.*, vol. 8(7):583–586, (1997). Abstract only.
Uno et al. *Chem. Lett.*, vol. 6: 1153–1156, (1987). Abstract only.
Greiner et al. *New J. Chem.*, vol. 13(3): 247–254, (1989). Abstract only.
Greiner et al. *Tetrahedron Lett.*, vol. 29(18):2193–2194, (1988). Abstract only.

*Primary Examiner*—John Kight
*Assistant Examiner*—Howard C. Lee
*Attorney, Agent, or Firm*—Millen, White, Zelano & Branigan, P.C.

[57] ABSTRACT

The invention relates to 1-C-perfluoroalkyl glucosides consisting essentially of a monosaccharide having an anomeric carbon directly linked to a perfluoroalkyl radical and a hydroxyl group. These glycosides are prepared by a process comprising: (a) reacting an aldonolactone with a hydroxyl protecting group; (b) reacting the product of step (a) with a compound of formula $R_F$-M in which $R_F$ represents a linear or branched perfluoroalkyl radical containing from 2 to 12 carbon atoms, and M represents Li or MgX, X being a halogen; and (c) liberating the hydroxyl group. The 1-C-perfluoroalkyl glycosides may be used as surfactants and as flame retardants.

15 Claims, No Drawings

1-C-PERFLOUROALKYL GLYCOSIDES, PREPARATION PROCESS AND USES THEREOF

FIELD OF THE INVENTION

The present invention relates to 1-C-perfluoroalkyl glycosides, to a process for their preparation and to their use in the field of surfactants.

BACKGROUND OF THE INVENTION

Perfluoroalkyl sugars are known for their surfactant properties and their capacity to transport oxygen. The latter property is useful in the biomedical field, in particular for the preparation of injectable blood substitutes.

Perfluoroalkyl sugars have been the subject of much research, among which mention may be made of:

the article by J. G. Riess and J. Greiner (Carbohydrates as Organic Raw Materials II, pp. 209–259, published by VCH (1993)) which describes perfluoroalkyl sugars comprising a hydrophilic head of glucidic nature, a junction component (for example ester, ether, amide or phosphoester), a hydrocarbon spacer and a perfluoroalkyl tail, the article by M. El Ghoul et al. (J. Fluorine Chem., vol. 59, pp. 107–112 (1992)) which proposes in particular N-[2-(F-alkyl)ethyl]lactosylamides, and patent application EP-A-375,610 which describes perfluoroalkylthioglycosides of formula $R_F$-E-S-saccharide in which $R_F$ represents a $C_1$–$C_{18}$ radical, E is a connecting group and the saccharide is an oligosaccharide containing 1 to 30 units of a $C_5$–$C_7$ sugar.

In the documents of the prior art which have just been mentioned, it is seen that the anomeric carbon bears, on the one hand, a substituent composed of a spacer arm and of a perfluoroalkyl radical, and, on the other hand, a hydrogen atom.

SUMMARY OF THE INVENTION

The present invention relates to novel perfluoroalkyl-C-glycosides, which glycosides are characterized in that they consist of a monosaccharide whose anomeric carbon is directly linked to a perfluoroalkyl radical and to a hydroxyl group.

Another subject of the invention relates to a process for the preparation of the said glycosides, comprising the following steps:

protection of the hydroxyl groups of an aldonolactone, reaction with a perfluoroalkyl reagent, and deprotection (liberation) of the said hydroxyl groups.

Another subject of the invention relates to the use of perfluoroalkyl-C-glycosides as surfactants and flame retardants.

The perfluoroalkyl-C-glycosides according to the invention consist of a monosaccharide whose carbon 1 bears a perfluoroalkyl radical and a hydroxyl group.

The perfluoroalkyl radical is generally chosen from linear or branched radicals containing from 2 to 12 carbon atoms, and preferably 2 to 8 carbon atoms.

The monosaccharide is generally a saccharide containing 4 to 7 carbon atoms. Preferably, the saccharide is erythrose, glucose, galactose, gulose or mannose, and advantageously glucose.

The 1-C-perfluoroalkyl glycosides according to the invention may be prepared by a process which consists in:

a—reacting an aldonolactone with an agent for protecting the hydroxyl groups, b—reacting the product of step a) with a compound of formula $R_F$-M in which $R_F$ represents a linear or branched perfluoroalkyl radical containing from 2 to 12 carbon atoms and M represents Li or MgX, X being a halogen, preferably Br, c—and deprotecting the said hydroxyl groups.

In carrying out step a), an aldonolactone containing from 4 to 7 carbon atoms, and preferably 6 carbon atoms, is generally used. Examples which may be mentioned are erythrono-1,4-lactone, glucono-1,5-lactone, glucoheptono-1,4-lactone, galactono-1,4-lactone, gulono-1,4-lactone and mannono-1,4-lactone. Preferably, glucono-1,5-lactone, and advantageously D-glucono-1,5-lactone, is used.

The protecting agent is generally chosen from compounds capable of forming ether and/or ketal groups with the free hydroxyl groups of the aldonolactone.

In order to obtain the ether derivatives, an alkyl halide, for example benzyl bromide or chloride, may be used.

In order to obtain the preferred persilyl derivatives, a trialkylsilyl halide, for example chlorotrimethylsilane, and/or a hexaalkyldisilazane, for example hexamethyldisilazane, may be used. A mixture of chlorotrimethylsilane and hexamethyldisilazane is preferably used.

The reaction is generally carried out in the presence of a base, for example pyridine or triethylamine. Pyridine is preferably used.

The reaction is generally carried out at a temperature of about 20° C. and for a period which may range from 1 to 6 hours.

In order to obtain the ketal derivatives, a carbonyl compound, for example acetone, or an enol ether, for example 2-methoxypropene, may be used. 2-Methoxypropene is preferably used.

The reaction is generally carried out in the presence of a solvent, for example acetone or dimethylformamide, and an acidic catalyst, for example para-toluenesulphonic acid, at a temperature of about 0° C. and for a period which may range from 20 to 48 hours.

In general, the protecting agent and the base are used in excess relative to the lactone.

The mixed ether/ketal derivatives may be obtained by successively carrying out the steps for preparing the ketal and the ether which are described above. Preferably, the derivative contains ether linkages in positions 2 and 3 and ketal linkages in positions 4 and 6 (in the case of glucono-1,5-lactone).

The product obtained after step a) may consist of one or more of the abovementioned derivatives. Preferably, the product is a persilyl derivative, a mixed (2,3-silyl ether, 4,6-ketal) derivative or a mixture of these derivatives (in the case of glucono-1,5-lactone).

The compound $R_F$-M used in step b) is generally obtained according to methods known to those skilled in the art, for example from R-M and $R_F$-Y, R representing an alkyl or aryl radical having 1 to 6 carbon atoms, $R_F$ having the meaning given above and Y being I or Br (see the article by D. J. Burton et al., Tetrahedron, vol. 48, No. 2, pp. 189–275, 1992).

In general, the ratio of the number of mole equivalents of $R_F$-M to the number of mole equivalents of the lactone varies from 1 to 1.5. The ratio is preferably equal to 1.1.

The reaction is generally carried out at a temperature of between −50° C. and −10° C., preferably of about −45° C., and for a period which may range from 1 to 6 hours.

The deprotection carried out in step c) is generally performed by hydrogenolysis (peralkyl derivatives, in particular perbenzyl derivatives) under conditions known to those skilled in the art, or by hydrolysis (ether, ketal and mixed derivatives).

In the case of ether derivatives such as persilyl derivatives, total hydrolysis may be carried out according to two alternatives.

The first alternative consists in reacting the product obtained in step b) with a fluoride such as a tetraalkylammonium fluoride or an alkali metal fluoride, for example caesium or potassium fluoride, in the presence of a solvent such as an alcohol. Tetrabutylammonium fluoride is preferably used.

The second alternative consists in dissolving the product obtained in step b) in an alcohol, for example methanol or ethanol, and in heating to reflux. Methanol is preferably used.

In the case of the ketal derivatives, total hydrolysis is generally carried out using an acidic resin, for example Amberlyst 15 wet H$^+$ marketed by Aldrich, advantageously in the presence of a water/water-miscible solvent mixture, preferably water/ethanol, heated to reflux.

In the case of the mixed derivatives, the hydrolysis may be selective or total.

In order to carry out selective hydrolysis, the mixed derivative is generally placed in contact with a fluoride under the conditions described above for the persilyl derivatives. The 1-C-perfluoroalkyl ketal derivative thus obtained may optionally be purified, for example by recrystallization. The final hydrolysis may be carried out using an acidic resin under the conditions described above for the ketal derivatives.

In order to carry out the total hydrolysis, the mixed derivative obtained in step b) is generally subjected to the action of an acidic resin under the conditions described above for the ketal derivatives. The 1-C-perfluoroalkyl glycoside thus obtained may optionally undergo a step of purification, for example by chromatography on silica gel.

The 1-C-perfluoroalkyl glycosides according to the invention are capable of many applications, for example as surfactants, in particular in the field of cosmetics, and as flame retardants.

The examples which follow allow the invention to be illustrated.

In the following examples, the analysis methods below are used:

Nuclear magnetic resonance (NMR)

The chemical shifts are expressed in ppm and the coupling constants J in Hz.

The compounds are dissolved in CDCl$_3$ (compounds 1 to 3), CD$_3$COCD$_3$ (compounds 4) and CD$_3$OD (compounds 5).

$^1$H NMR: Bruker machine; 250 MHz (compounds 1 to 4) and 500 MHz (compounds 5)

$^{13}$C NMR: Bruker machine; 62.89 MHz (compounds 1 to 4) and 125 MHz (compounds 5)

$^{19}$F NMR: Bruker machine; 235.36 MHz

Mass spectrometry (MS): Jeol D300 machine; 70 eV; electron impact.

The values are expressed in atomic mass units (m/z) and the intensities in % of the base peak are indicated in parentheses.

Infrared (IR) spectrography; KBr disc.

The values are expressed in cm$^{-1}$. The intensities of the bands, in parentheses, are noted w (weak), m (medium), s (strong) and vs (very strong).

Optical rotation.

Quantitative elemental analysis.

EXAMPLE 1 a) Preparation of 4,6-O-isopropylidene-2,3-di-O-trimethylsilyl-D-glucono-1,5-lactone (1)

To a round-bottomed flask containing 100 ml of anhydrous dimethylformamide, 84 mg of para-toluene-sulphonic acid and 5 g (28 mmol) of D-glucono-1,5-lactone, maintained at 0° C., are added dropwise 5.4 ml (56 mmol) of 2-methoxypropene.

After 24 hours at 0° C., 11.3 ml (140 mmol) of pyridine are added and 11 ml (84 mmol) of chlorotrimethylsilane are added dropwise.

After stirring for 2 hours at 20°–25° C., the contents of the flask are poured into ice-water, the pH needing to remain basic. After extraction of the aqueous phase with ether (2×50 ml), the organic phases are combined, dried (sodium sulphate), filtered and evaporated. The residue obtained is subjected to a step of chromatography on silica gel (petroleum ether/ethyl acetate 95/5; v/v).

6.6 g of 4,6-O-isopropylidene-2,3-di-O-trimethylsilyl-D-glucono-1,5-lactone (compound 1) are recovered in the form of a white solid, i.e. a yield of 65% calculated on the basis of the mass of starting D-glucono-1,5-lactone.

The characteristics of compound 1 are as follows:

melting point: 80° C.

$^1$H NMR: 0.14 (s, 9H, Si(CH$_3$)$_3$); 0.20 (s, 9H, Si(CH$_3$)$_3$); 1.43 (s, 3H, CH$_3$); 1.50 (s, 3H, CH$_3$); 3.66–4.10 (m, 6H, H-2, H-3, H-4, H-5, H-6a, H-6e).

$^{13}$C NMR: 0.1 (Si(CH$_3$)$_3$); 0.7 (Si(CH$_3$)$_3$); 18.8 (C(CH$_3$)); 28.7 (C(CH$_3$)); 61.5 (C-6); 68.7 (C-5); 72.6 (C-4); 75.8 (C-3 and C-2); 99.7 (Cq isopropylidene); 170.0 (C-1).

MS: 362 (M$^+$, 6); 342 (25); 304 (27); 289 (14); 215 (68); 157 (53); 73 (100).

IR: 2961 (w); 1768 (s); 1253 (m); 1140 (m); 852 (s).

b) Preparation of 1-C-perfluorobutyl-4,6-O-isopropylidene-2,3-di-O-trimethylsilyl-α-D-glucopyranose(3a)

To a round-bottomed flask containing a solution of perfluorobutyl iodide (6.6 mmol in 20 ml of anhydrous ether), placed at −45° C. and in the absence of light, are added dropwise 2.2 ml (6.6 mmol) of ethylmagnesium bromide.

After 30 minutes, 2 g (5.5 mmol) of compound 1 obtained in step a) dissolved in 3 ml of ether are added dropwise. The temperature is allowed to rise to −10° C. Once the reaction is complete, saturated ammonium chloride solution is added until the pH is neutral.

The aqueous phase is recovered and extracted with ether (2×100 ml). The organic phases are combined, dried (magnesium sulphate) and evaporated. The solid residue obtained is chromatographed on silica gel (95/5 petroleum ether/ethyl acetate; v/v).

The 1-C-perfluorobutyl-4,6-O-isopropylidene-2,3-di-O-trimethylsilyl-α-D-glucopyranose (compound 3a) is recovered in a yield equal to 96% calculated on the basis of the mass of starting compound 1.

The characteristics of compound 3a are as follows:

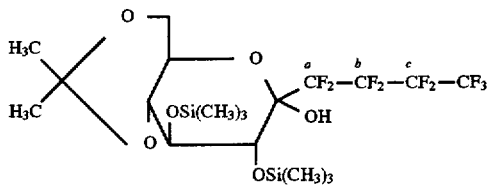

melting point: 78° C.

$^1$H NMR: 0.14 (s, 9H, Si(CH$_3$)$_3$); 0.19 (s, 9H, Si(CH$_3$)$_3$); 1.41 (s, 3H, CH$_3$); 1.48 (s, 3H, CH$_3$); 3.44 (dd, 1H, J$_{4,3}$= J$_{4,5}$=9.1, H-4); 3.62 (dd, 1H, J$_{3,4}$=9.1, J$_{3,2}$=7.6, H-3); 3.72–3.79 (m, 2H, H-5, H-6e); 3.89 (dd, 1H, J$_{6a,6e}$=8.8, J$_{6a,5}$=4.2, H-6a); 4.04 (dd, 1H, J$_{2,3}$=7.6, J$_{2,F}$=1.4, H-2); 4.59 (bs, 1H, OH).

$^{13}$C NMR: 0.5 (Si(CH$_3$)$_3$); 1.0 (Si(CH$_3$)$_3$); 18.8 (C(CH$_3$)); 28.9 (C (CH$_3$)); 61.5 (C-6); 64.0 (C-5); 72.3 (C-4); 73.5 (C-2); 75.9 (C-3); 97.8 (t, $^2$J$_{C,F}$=26.0, C-1); 99.5 (Cq isopropylidene).

$^{19}$F NMR: −81.35 (t, 3F, J=10.2, CF$_3$); −120.61 (dm, 1F, J$_{AB}$=297.6, CFa); −120.83 (multiplet, 2F, CF$_2$b); −122.18 (dm, 1F, J$_{AB}$=297.6, CFa'); −125.33 (bd, 1F, J$_{AB}$=305.2, CFc); −127.38 (dm, 1F, J$_{AB}$=305.2, CFc').

MS: 582 (M$^+$, 17); 434 (5); 345 (14); 204 (27); 144 (44); 103 (32); 73 (100).

IR: 3537 (w); 2972 (w); 1379 (m); 1215 (s); 1140 (s); 852 (s).

$[\alpha]_D^{20}$=+97° (c=1.03; CHCl$_3$).

Analysis: C$_{19}$H$_{31}$O$_6$Si$_2$F$_9$ (582.61)

Theory: C: 39.17 H: 5.32

Calculated: C: 39.23 H: 5.37 c) Preparation of 1-C-perfluorobutyl-4,6-O-isopropylidene-α-D-glucopyranose (4a)

To a round-bottomed flask containing 0.91 g (1.16 mmol) of compound 3a obtained in the above step dissolved in 6 ml of methanol are added 1.16 mmol of tetrabutylammonium fluoride at 20°–25° C.

After stirring for two hours, the solvent is evaporated off. The residue obtained is recrystallized from toluene. The 1-C-perfluorobutyl-4,6-O-isopropylidene-α-D-glucopyranose (compound 4a) is recovered in a yield of 96% calculated on the basis of the mass of starting compound 3a.

The characteristics of compound 4a are as follows:

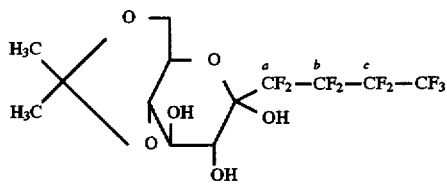

melting point: 177° C.

$^1$H NMR: 1.33 (s, 3H, CH$_3$); 1.48 (s, 3H, CH$_3$); 3.52–3.81 (multiplet, 5H, H-3, H-4, H-5, H-6ax, H-6eq); 3.91 (d, 1H, J=8.0, H-2); 4.56 (bs, 1H, OH); 4.98 (bs, 1H, OH); 6.14 (bs, 1H, anomeric OH).

$^{13}$C NMR: 19.4 (C(CH$_3$)); 29.5 (C(CH3)); 62.5 (C-6); 65.6 (C-5); 72.5 (C-4); 73.2 (C-2); 73.6 (C-3); 98.8 (t, $^2$J$_{CF}$=26.0, C-1); 100.2 (Cq isopropylidene).

$^{19}$F NMR: −80.67 (t, 3F, J=9.0, CF$_3$); −120.16 (multiplet, 4F, CF2a, CF$_2$b); −124.83 (dm, 1F, J$_{AB}$=290.0, CFc); −125.74 (dm, 1F, J$_{AB}$=290.0, CFc').

MS: 438 (M$^+$, trace); 423 (60); 315 (9); 299 (7); 109 (14); 73 (43); 59 (100).

IR: 3412 (b); 2997 (w); 1390 (w); 1244 (s); 1140 (s); 713 (m).

$[\alpha]_D^{19}$=+10.0° (c=0.45; CH$_3$COCH$_3$).

Analysis: C$_{13}$H$_{15}$O$_6$F$_9$ (438.25)

Theory: C: 35.62 H: 3.45

Calculated: C: 35.56 H: 3.15 d) Preparation of 1-C-perfluorobutyl-α-D-glucose (5a)

To a round-bottomed flask over which is mounted a condenser, containing 11.9 mmol of compound 4a obtained in the above step dissolved in 60 ml of an ethanol/water (95/5; v/v) mixture are added 1.15 g of acidic resin (Amberlyst 15 wet H$^+$; Aldrich).

After stirring for 2 hours in refluxing ethanol, the contents of the flask are filtered. The organic phase is recovered and evaporated. The residue obtained, chromatographed on silica gel (20/80 petroleum ether/ethyl acetate; v/v), gives 1-C-perfluorobutyl-D-glucose (compound 5a) in a yield of 95% calculated on the basis of the mass of starting compound 4a.

Compound 5a consists of a mixture of a pyran form and a furan form whose proportions vary as a function of the NMR solvent used:

furan: pyran=30:70 (CD$_3$COCD$_3$)

furan: pyran=80:20 (CD$_3$OD)

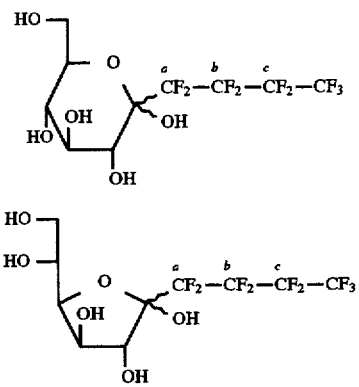

melting point: 140°–142° C.

$^1$H NMR: 3.68 (dd, 1H, J$_{6,6}$=11.5, J$_{6,5}$=6.0, H-6); 3.85 (dd, 1H, J$_{6',6}$=11.5, J$_{6',5}$=3.2, H-6'); 4.00 (m, 1H, H-5); 4.18, (dd, 1H, J$_{4,5}$=8.1, J$_{4,3}$=4.9, H-4); 4.37 (dd, 1H, J$_{3,4}$=4.9, J$_{3,2}$=2.8, H-3); 4.42 (d, 1H, J$_{2,3}$=2.8, H-2).

$^{13}$C NMR:

Furan form: 64.9 (C-6); 71.4 (C-5); 78.1 (C-3); 79.7 (C-2); 80.1 (C-4); 103.0 (t, $^2$J$_{C,F}$=29.0, C-1); 110.8 (ts, J$_{1,F}$=270, J$_{2,F}$=39, Cc); 113.0 (tq, J$_{1,F}$=269, J$_{2,F}$=30, Cb); 115.5 (tt, J$_{1,F}$=261, J$_{2,F}$=30, Ca); 119.3 (qt, J$_{1,F}$=288, J$_{2,F}$=34, CF$_3$).

Pyran form: 62.7 (C-6); 71.0 (C-5); 72.8 (C-3); 75.3 (C-2); 76.2 (C-4); 98.6 (t, $^2$J$_{C,F}$=24.0, C-1).

$^{19}$F NMR: −80.74 (t, 3F, $^4$J=9.0, CF$_3$); −119.83 (multiplet, 2F, CF$_2$a); −120.50 (multiplet, 2F, CF$_2$b); −125.41 (multiplet, 2F, CF$_2$c).

MS: 398 (M$^+$, trace); 289 (17); 259 (16); 131 (34); 109 (32); 73 (100).

IR: 3601 (m); 3474 (b); 3387 (b); 2961 (m); 1228 (vs); 1140 (vs); 1078 (m).

$[\alpha]_D^{22}$=+13.7° (c=0.46; CH$_3$OH)

Analysis: C$_{10}$H$_{11}$O$_6$F$_9$ (398.18)

Theory: C: 30.15 H: 2.76

Calculated: C: 30.59 H: 2.59

EXAMPLE 2

The process is carried out under the conditions of Example 1 modified in that perfluorohexyl iodide is used. In this example, the perfluoroalkyl radical is noted:

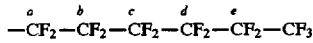

After step b, 1-C-perfluorohexyl-4,6-O-isopropylidene-2,3-O-trimethylsilyl-α-D-glucopyranose (compound 3b) is obtained, the characteristics of which are as follows:

melting point: 78° C.

$^1$H NMR: 0.16 (s, 9H, Si(CH$_3$)$_3$); 0.18 (s, 9H, Si(CH$_3$)$_3$); 1.41 (s, 3H, CH$_3$); 1.49 (s, 3H, CH$_3$); 3.44 (dd, 1H, J$_{4,3}$=J$_{4,5}$=9.1, H-4); 3.64 (dd, 1H, J$_{3,4}$=9.1, J$_{3,2}$=7.6, H-3); 3.69–3.84 (m, 2H, H-5, H-6e); 3.89 (dd, 1H, J$_{6a,6e}$=8.8, J$_{6a,5}$=4.2, H-6a); 4.04 (dd, 1H, J$_{2,3}$=7.6, J$_{2,F}$=1.6, H-2); 4.62 (bs, 1H, OH).

$^{13}$C NMR: 0.5 (Si(CH$_3$)$_3$); 1.0 (Si(CH$_3$)$_3$); 18.8 (C(CH$_3$)); 28.9 (C(CH$_3$)); 61.5 (C-6); 64.0 (C-5); 72.4 (C-4); 73.5 (C-2); 75.9 (C-3); 97.8 (t, $^2$J$_{C,F}$=25.0, C-1); 99.5 (Cq isopropylidene).

$^{19}$F NMR: −81.35 (t, 3F, J=9.0, CF$_3$); −119.79 (multiplet, 4F, CF$_2$a, CF$_2$b); −122.10 (multiplet, 2F, CF$_2$c); −123.20 (multiplet, 2F, CF$_2$d); −126.55 (multiplet, 2F, CF$_2$e).

MS: 682 (M$^+$, 48); 445 (26); 204 (42); 144 (100); 103 (60); 73 (78).

IR: 3549 (w); 2947 (w); 1240 (s); 1153 (m); 852 (s).

[α]$_D^{20}$=+8.0° (c=1.1; CHCl$_3$).

Analysis: C$_{21}$H$_{31}$O$_6$Si$_2$F$_{13}$ (682.63)

Theory: C: 36.95 H: 4.54

Calculated: C: 37.21 H: 4.52

After step c, 1-C-perfluorohexyl-4,6-O-isopropylidene-α-D-glucopyranose (compound 4b) is obtained, the characteristics of which are as follows:

melting point: 171° C.

$^1$H NMR: 1.33 (s, 3H, CH$_3$); 1.43 (s, 3H, CH$_3$); 3.53 (dd, 1H, J=9.5, J=1.5, H-4); 3.65–3.80 (m, 4H, H-3, H-5, H-6a, H-6e); 3.86 (dd, 1H, J=8.0, J=1.5, H-2); 4.43 (bs, 1H, OH); 4.87 (bs, 1H, OH); 5.97 (bs, 1H, anomeric OH).

$^{13}$C NMR: 19.2 (C(CH$_3$)); 29.2 (C(CH$_3$)); 62.1 (C-6); 65.1 (C-5); 72.2 (C-4); 72.8 (C-2); 73.0 (C-3); 98.3 (t, $^2$J$_{C,F}$=26.0, C-1); 99.9 (Cq isopropylidene); 106.8–124.7 (C$_6$F$_{13}$).

$^{19}$F NMR: −80.99 (t, 3F, J=9.0, CF$_3$); −119.01 (multiplet, 4F, CF$_2$a, CF$_2$b); −121.04 (multiplet, 2F, CF$_2$c); −122.15 (multiplet, 2F, CF$_2$d); −125.63 (multiplet, 2F, CF$_2$e).

MS: 538 (M$^+$, 2); 523 (38); 137 (23); 95 (22); 69 (100).

IR: 3425 (b); 2910 (w); 1390 (w); 1203 (s); 1153 (s).

[α]$_D^{19}$=+7.9° (c=0.39; CH$_3$COCH$_3$).

Analysis: C$_{15}$H$_{15}$O$_6$F$_{13}$ (538.27)

Theory: C: 33.45 H: 2.78

Calculated: C: 33.50 H: 2.50

After step d, 1-C-perfluorohexyl-D-glucose (compound 5b) is obtained in a yield of 95% calculated on the basis of the mass of starting compound 4b.

The characteristics of compound 5b are as follows:

$^1$H NMR: 3.68 (dd, 1H, J$_{6,6}$=11.5, J$_{6,5}$=6.5, H-6); 3.84 (dd, 1H, J$_{6',6}$=11.5, J$_{6',5}$=3.2, H-6'); 3.99 (m, 1H, H-5); 4.17 (dd, 1H, J$_{4,5}$=8.2, J$_{4,3}$=4.9, H-4); 4.36 (dd, 1H, J$_{3,4}$=4.9, J$_{3,2}$=2.8, H-3); 4.42 (d, 1H, J$_{2,3}$=2.8, H-2).

$^{13}$C NMR:

Furan form: 64.9 (C-6); 71.4 (C-5); 78.2 (C-3); 79.8 (C-2); 80.2 (C-4); 103.1 (t, $^2$J$_{C,F}$=28.4, C-1).

Pyran form: 62.7 (C-6); 71.1 (C-5); 72.9 (C-3); 75.3 (C-2); 76.2 (C-4); 98.8 (t, $^2$J$_{C,F}$=25.0, C-1).

$^{19}$F NMR: −80.74 (t, 3F, J=9.0, CF$_3$); −119.43 (multiplet, 4F, CF$_2$a, CF$_2$b); −121.06 (multiplet, 2F, CF$_2$c); −122.19 (multiplet, 2F, CF$_2$d); −125.04 (d, 1F, J$_{AB}$=310.0, CF$_2$e); −126.05 (d, 1F, J$_{AB}$=310.0, CF$_2$e').

MS: 498 (M$^+$, trace); 419 (10); 389 (22); 359 (17); 131 (28); 109 (41); 91 (20); 73 (100).

IR: 3601 (w); 3387 (s); 2947 (w); 1203 (s); 1140 (s).

[α]$_D^{19}$=+10.5° (c=1.08; CH$_3$OH)

Analysis: C$_{12}$H$_{11}$O$_6$F$_{13}$ (498.20)

Theory: C: 28.91 H: 2.20

Calculated: C: 28.84 H: 2.01

EXAMPLE 3

The process is carried out under the conditions of Example 1 modified in that perfluorooctyl iodide is used. In this example, the perfluoroalkyl radical is noted:

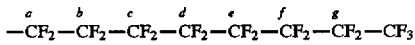

After step b, 1-C-perfluorooctyl-4,6-O-isopropylidene-2,3-O-trimethylsilyl-α-D-glucopyranose (compound 3c) is obtained, the characteristics of which are as follows:

melting point: 98°–100° C.

$^1$H NMR: 0.12 (s, 9H, Si(CH$_3$)$_3$); 0.14 (s, 9H, Si(CH$_3$)$_3$); 1.38 (s, 3H, CH$_3$); 1.43 (s, 3H, CH$_3$); 3.41 (dd, 1H, J$_{4,3}$=9.11 J$_{4,5}$=8.8, H-4); 3.61 (dd, 1H, J$_{3,4}$=9.1, J$_{3,2}$=7.6, H-3); 3.66–3.80 (m, 2H, H-5, H-6e); 3.85 (dd, 1H, J=8.8, J=4.2, H-6a); 4.01 (dd, 1H, J$_{2,3}$=7.6, J$_{2,F}$=1.5, H-2); 4.67 (bs, 1H, OH)

$^{13}$C NMR: 0.4 (Si(CH$_3$)$_3$); 0.9 (Si(CH$_3$)$_3$); 18.8 (C(CH$_3$)); 28.8 (C(CH$_3$)); 61.5 (C-6); 64.0 (C-5); 72.3 (C-4); 73.5 (C-2); 75.9 (C-3); 97.8 (t, $^2$J$_{C,F}$=26.0, C-1); 99.5 (Cq isopropylidene).

$^{19}$F NMR: −81.31 (t, 3F, J=9.0, CF$_3$); −120.31 (multiplet, 4F, CF$_2$a, CF$_2$b); −122.05 (multiplet, 6F, CF$_2$c, CF$_2$d, CF$_2$e); −123.11 (multiplet, 2F, CF$_2$f); −126.55 (multiplet, 2F, CF$_2$g).

MS: 782 (M$^+$, 2); 767 (17); 601 (12); 545 (23); 204 (38); 159 (29); 131 (56); 103 (36); 73 (100).

IR: 3387 (b); 2947 (m); 1203 (vs); 857 (s); 663 (w).

[α]$_D^{18}$=+10.6° (c=0.77; CH$_3$COCH$_3$).

Analysis: C$_{23}$H$_{31}$O$_6$Si$_2$F$_{17}$(782.65)

Theory: C: 35.26 H: 3.96

Calculated: C: 34.93 H: 3.88

After step c, 1-C-perfluorooctyl-4,6-O-isopropylidene-α-D-glucopyranose (compound 4c) is obtained in a yield of 99% calculated on the basis of the mass of starting compound 3c.

The characteristics of compound 4c are as follows:

melting point: 162° C.

$^1$H NMR: 1.34 (s, 3H, CH$_3$); 1.49 (s, 3H, CH$_3$); 3.57 (m, 1H, H-4); 3.75 (multiplet, 4H, H-3, H-5, H-6e, H-6a); 3.91 (d, 1H, J=8.4, H-2); 4.58 (bs, 1H, OH); 4.96 (bs, 1H, OH); 6.10 (bs, 1H, anomeric OH).

$^{13}$C NMR: 19.4 (C(CH$_3$)); 29.8 (C(CH$_3$)); 62.5 (C-6); 65.6 (C-5); 72.6 (C-4); 73.1 (C-2); 73.6 (C-3); 98.8 (t, $^2$J$_{C,F}$=25.0, C-1); 100.2 (Cq isopropylidene).

$^{19}$F NMR: −80.74 (t, 3F, J=9.0, CF$_3$); −118.93 (multiplet, 4F, CF$_2$a, CF$_2$b); −121-09 (multiplet, 6F, CF$_2$c, CF$_2$d, CF$_2$e); −122.20 (multiplet, 2F, CF$_2$f); −125.69 (multiplet, 2F, CF$_2$g).

MS: 623 (68); 131 (24); 81 (31); 73 (39); 69 (64); 59 (100).

IR: 3412 (b); 2997 (w); 1203 (s); 1153 (s); 1078 (m).

$[\alpha]_D^{19}$=+6.5° (c=0.63; $CH_3COCH_3$).

After step d, 1-C-perfluorooctyl-D-glucose (compound 5c) is obtained in a yield of 95% calculated on the basis of the mass of starting compound 4c.

The characteristics of compound 5c are as follows:

melting point: 209° C.

$^1H$ NMR: 3.68 (dd, 1H, $J_{6,6'}$=11.5, $J_{6,5}$=6.0, H-6); 3.84 (dd, 1H, $J_{6',6}$=11.5, $J_{6',5}$=3.2, H-6'); 3.99 (m, 1H, H-5); 4.17 (dd, 1H, $J_{4,5}$=8.2, $J_{4,3}$=4.9, H-4); 4.36 (dd, 1H, $J_{3,4}$=4.9, $J_{3,2}$=2.8, H-3); 4.42 (d, 1H, $J_{2,3}$=2.8, H-2).

$^{13}C$ NMR

Furan form: 64.9 (C-6); 71.4 (C-5); 78.1 (C-3); 79.8 (C-2); 80.2 (C-4); 103.1 (t, $^2J_{C,F}$=28.8, C-1).

Pyran form: 62.7 (C-6); 71.1 (C-5); 72.9 (C-3); 75.3 (C-2); 76.2 (C-4); 98.8 (t, $^2J_{C,F}$=24.0, C-1).

$^{19}F$ NMR: –80.68 (t, 3F, J=9.0, $CF_3$); –119.42 (multiplet, 4F, $CF_2$a, $CF_2$b); –120.94 (multiplet, 6F, $CF_2$c, $CF_2$d, $CF_2$e); –122.16 (multiplet, 2F, $CF_2$f); –125.16 (multiplet, 2F, $CF_2$g).

MS: 562 (13); 519 (50); 139 (25); 109 (35); 73 (100).

IR: 3601 (w); 3387 (s); 2961 (w); 1203 (s); 1140 (s); 1078 (m).

$[\alpha]_D^{19}$=+7.9° (c=0.43; $CH_3OH$)

Analysis: $C_{14}H_{11}O_6F_{17}$ (598.22)

Theory: C: 28.09 H: 1.83

Calculated: C: 28.25 H: 2.01

EXAMPLE 4

Preparation of 4,6-O-isopropylidene-2,3-di-O-trimethylsilyl-D-glucono-1,5-lactone (1) and tetra-O-trimethylsilyl-D-glucono-1,5-lactone (2)

To a round-bottomed flask containing 65 ml of anhydrous dimethylformamide, 60 mg of para-toluenesulphonic acid and 3.5 g (19.6 mmol) of D-glucono-1,5-lactone, maintained at 0° C., are added dropwise 3.8 ml (39.2 mmol) of 2-methoxypropene.

After 24 hours at 0° C., 7.9 ml (98 mmol) of pyridine are added and 7.7 ml (5.9 mmol) of chlorotrimethylsilane are added dropwise.

After stirring for 2 hours at 20°–25° C., the contents of the flask are poured into ice-water, the pH needing to remain basic. After extraction of the aqueous phase with ether (2×50 ml), the organic phases are combined, dried (sodium sulphate), filtered and evaporated. The residue obtained contains 4,6-O-isopropylidene-2,3-di-O-trimethylsilyl-D-glucono-1,5-lactone (compound 1, major) and tetra-O-trimethylsilyl-D-glucono-1,5-lactone (compound 2).

1C-Perfluoroalkylation of compounds 1 and 2

To a round-bottomed flask containing a solution of perfluorobutyl iodide (23.5 mmol in 80 ml of anhydrous ether), placed at –45° C. and in the absence of light, are added dropwise 23.5 mmol of ethylmagnesium bromide.

After 30 minutes, 19.6 mmol of the residue obtained in the above step dissolved in 20 ml of ether are introduced dropwise. The temperature is allowed to rise to –10° C. and saturated ammonium chloride solution is added until the pH is neutral.

The aqueous phase is recovered and extracted with ether (2×100 ml). The organic phases are combined, dried (magnesium sulphate) and evaporated. A solid residue is obtained.

Preparation of 1-C-perfluorobutyl-D-glucose

To a round-bottomed flask, over which is mounted a condenser, containing 18.7 mmol of the solid residue obtained in the above step dissolved in 90 ml of an ethanol/water (95/5; v/v) mixture are added 1.7 g of acidic resin (Amberlyst 15 wet $H^+$; Aldrich).

After stirring for 2 hours in the refluxing ethanol/water mixture, the contents of the flask are filtered. The organic phase is recovered and evaporated. The residue obtained, chromatographed on silica gel (20/80 petroleum ether/ethyl acetate; v/v), gives 6.26 g of 1-C-perfluorobutyl-D-glucose (compound 5a), i.e. a yield of 80% calculated on the basis of the starting D-glucono-1,5-lactone.

EXAMPLE 5

Preparation of tetra-O-trimethylsilyl-D-glucono-1,5-lactone (2)

To a round-bottomed flask containing 5 g (28 mmol) of D-glucono-1,5-lactone dissolved in 47 ml of pyridine are added 23.6 ml (112 mmol) of hexamethyldisilazane and 7 ml (56 mmol) of trimethylsilyl chloride.

After stirring for 2 hours at 20°–25° C., 150 ml of pentane are added and the contents of the flask are filtered over Celite in order to remove the salts. The filtrate is recovered and evaporated. 13 g of tetra-O-trimethylsilyl-D-glucono-1,5-lactone (compound 2) are obtained, i.e. a yield of 100% calculated on the basis of the mass of starting D-glucono-1,5-lactone.

Preparation of 1-C-perfluorohexyl-D-glucose (5b)

To a round-bottomed flask containing a solution of perfluorohexyl iodide (7.7 mmol in 35 ml of anhydrous ether), placed at –45° C. and in the absence of light, are added dropwise 2.76 ml (7.7 mmol) of ethylmagnesium bromide.

After 30 minutes, 3 g (6.43 mmol) of the abovementioned compound 2 dissolved in 10 ml of ether are introduced dropwise. The temperature is allowed to rise to –10° C. and saturated ammonium chloride solution is added until the pH is neutral.

The aqueous phase is recovered and extracted with ether (2×100 ml). The organic phases are combined, dried (magnesium sulphate) and filtered.

The filtrate is recovered and evaporated. 4.81 g of the corresponding 1-C-perfluorohexyl derivative are obtained, i.e. a yield of 95% calculated on the basis of the mass of starting compound 2.

This derivative is heated in refluxing methanol (20 ml) for 4 hours.

The residue obtained after evaporation of the methanol is chromatographed on silica gel (20/80 petrol ether/ethyl acetate; v/v). 2.93 g of 1-C-perfluorohexyl-D-glucose (compound 5b) are recovered, i.e. a yield of 92% calculated on the basis of the mass of starting D-glucono-1,5-lactone employed.

Examples of using the perfluoroalkyl-C-glycosides as surfactants and fire retardants involve employing the glycosides in conventional amounts for these purposes. Likewise, the glycosides can be used for other purposes as mentioned in the prior art, e.g., for the preparation of injectable blood substrates.

The preceding examples can be repeated with similar success by substituting the generically or specifically described reactants and/or operating conditions of this invention for those used in the preceding examples.

The entire disclosure of all applications, patents and publications, cited above, and of corresponding French application 96/07692, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

We claim:

1. A perfluoroalkyl-C-glycoside, consisting essentially of a monosaccharide having an anomeric carbon directly linked to a perfluoroalkyl radical and to a hydroxyl group.

2. A perfluoroalkyl-C-glycoside according to claim 1, wherein the monosaccharide is a saccharide containing 4 to 7 carbon atoms.

3. A perfluoroalkyl-C-glycoside according to claim 1, wherein the saccharide is glucose, galactose, gulose or mannose.

4. A perfluoroalkyl-C-glycoside according to claim 1, wherein the perfluoroalkyl radical is linear or branched and contains from 2 to 12 carbon atoms.

5. A process for the preparation of a perfluoroalkyl-C-glycoside according to claim 1, comprising:

a—reacting an aldonolactone with an hydroxyl-protecting agent, b—reacting the resultant product of step a) with a compound of formula $R_F$-M, wherein $R_F$ represents a linear or branched perfluoroalkyl radical containing from 2 to 12 carbon atoms, and M represents Li or MgX, X being a halogen, c–liberating the hydroxyl groups in the resultant product of step b).

6. A process according to claim 5, wherein the aldonolactone contains from 4 to 7 carbon atoms.

7. A process according to claim 5, wherein the aldonolactone is erythrono-1,4-lactone, glucono-1,5-lactone, glucoheptono-1,4-lactone, galactono-1,4-lactone, gulono-1,4-lactone or mannono-1,4-lactone.

8. A process according to claim 5, wherein the hydroxyl-protecting agent is a compound capable of forming at least one of ether and ketal groups with the free hydroxyl groups of the aldonolactone.

9. A process according to claim 8, wherein the hydroxyl-protecting agent is an alkyl halide, a trialkylsilyl halide, a carbonyl compound or an enol ether.

10. A process according to claim 5, wherein the liberating of the hydroxyl groups is carried out by hydrogenolysis or by hydrolysis.

11. A process according to claim 10, wherein total hydrolysis is employed and is conducted with a fluoride, an alcohol heated to reflux or an acidic resin.

12. A process according to claim 10, wherein selective hydrolysis of ether groups is carried out using a fluoride.

13. A cosmetic composition comprising an amount effective to impart surfactant activity of a perfluoroalkyl-C-glycoside according to claim 1.

14. A flame retardant composition comprising a perfluoroalkyl-C-glycoside according to claim 1.

15. A perfluoroalkyl-C-glycoside according to claim 1, selected from the group consisting of:

1-C-perfluorobutyl-4,6-O-isopropylidene-α-D-glucopyranose;

1-C-perfluorobutyl-D-glucose;

1-C-perfluorobutyl-α-D-glucose;

1-C-perfluorohexyl-D-glucose; and

1-C-perfluorooctyl-D-glucose.

* * * * *

UNITED STATES PATENT AND TRADEMARK OFFICE
CERTIFICATE OF CORRECTION

Page 1 of 2

PATENT NO. : 5,786,469
DATED : July 28, 1998
INVENTOR(S) : Sandrine LAVAIRE et al.

It is certified that error appears in the above-identified patent and that said Letters Patent is hereby corrected as shown below:

In the Title:

Change "1-C-PERFLOUROALKYL" to --1-C-PERFLUOROALKYL--.

In the Abstract:

Line 1, change "glucosides" to --glycosides--.
Line 10, change "group" to --groups--.
Column 1, line 1:  change "1-C-PERFLOUROALKYL" to --1-C-PERFLUOROALKYL--.

Column 5, line 60: change "29.5 (C($\underline{C}$H3))" to --29.5 (C(CH$_3$))--.
Column 5, line 64: change "CF2a" to --CF$_{2a}$--.

Column 8, line 4:  change "CF$_2$C" to --CF$_2$c--.
Column 8, line 29: change "(dd, 1H, J$_{4.3}$=9.11" to --(dd, 1H, J$_{4,3}$=9.1)--.
Column 8, line 32: change "(dd, 1H, J$_{23}$=7.6" to --(dd, 1H, J$_{2,3}$=7.6)--.

UNITED STATES PATENT AND TRADEMARK OFFICE
CERTIFICATE OF CORRECTION

PATENT NO. : 5,786,469
DATED : July 28, 1998
INVENTOR(S) : Sandrine LAVAIRE, et. al.

It is certified that error appears in the above-identified patent and that said Letters Patent is hereby corrected as shown below:

Column 9, line 15: change "Puran form" to --Furan form--.
Column 9, line 18: change "(t, $^2J_{C.F}$)=24.0, C-1)" to --(t, $^2J_{C:F-}$=24.0, C-1)--.

Signed and Sealed this

Fourth Day of April, 2000

Attest:

Q. TODD DICKINSON

Attesting Officer      Director of Patents and Trademarks